United States Patent [19]

Moulton et al.

[11] 4,427,802

[45] Jan. 24, 1984

[54] HETEROCYCLIC MULTIFUNCTIONAL AMINE ADDUCTS AND CURABLE COMPOSITIONS CONTAINING THE SAME

[75] Inventors: Richard J. Moulton, Clayton; John D. Neuner, Pittsburg, both of Calif.

[73] Assignee: Hexcel Corporation, San Francisco, Calif.

[21] Appl. No.: 286,897

[22] Filed: Jul. 27, 1981

[51] Int. Cl.$^3$ .......................... C08K 3/04; C08K 3/36; C08G 59/00; C08G 59/50

[52] U.S. Cl. .................................... 523/222; 523/444; 523/468; 525/110; 525/113; 528/116; 528/117; 528/118; 264/22; 264/26

[58] Field of Search ................. 528/116, 117, 118; 523/222, 468, 444, 446; 264/22, 26; 525/110, 113

[56] References Cited

U.S. PATENT DOCUMENTS

| | | | |
|---|---|---|---|
| 3,907,623 | 9/1975 | Dowbenko | 428/415 |
| 3,950,451 | 4/1976 | Suzuki et al. | 525/490 |
| 4,017,438 | 4/1977 | Jerabek et al. | 428/418 |
| 4,101,497 | 7/1978 | Charves et al. | 525/453 |
| 4,146,520 | 3/1979 | Bierwirth et al. | 525/180 |
| 4,148,772 | 4/1979 | Marchetti et al. | 525/523 |
| 4,148,950 | 4/1979 | Brindell et al. | 523/402 |
| 4,195,152 | 3/1980 | Floyd | 528/87 |
| 4,289,869 | 9/1981 | Zengel et al. | 528/117 |

FOREIGN PATENT DOCUMENTS

| | | | |
|---|---|---|---|
| 749989 | 1/1967 | Canada | 528/116 |

*Primary Examiner*—Theodore Morris
*Assistant Examiner*—Herbert J. Lilling
*Attorney, Agent, or Firm*—Oblon, Fisher, Spivak, McClelland & Maier

[57] ABSTRACT

A curable composition, and composites comprising (A) an epoxy resin and (B) a heterocyclic compound prepared by reacting at least one aromatic or aliphatic polyamine compound having at least two amine groups, which are separated by no more than one carbon atom, with at least one carbonyl-containing compound selected from the group consisting of aldehydes and ketones.

26 Claims, No Drawings

HETEROCYCLIC MULTIFUNCTIONAL AMINE ADDUCTS AND CURABLE COMPOSITIONS CONTAINING THE SAME

BACKGROUND OF THE INVENTION

1. Field of the Invention

This invention relates to heterocyclic multifunctional amine adducts, methods of preparing the same, curable compositions containing the same and methods of curing the same.

2. Description of the Prior Art

Polymerized resins are employed for many commercial and military applications. These compositions provide lightweight products which have a high strength to weight ratio and good durability. Polymerized compositions are employed for many end uses which include molding compounds, adhesives, laminates made by bonding layers of impregnated reinforcement together and other such molded products. Particularly important is the use of polymerized epoxy resin in combination with reinforcements for aircraft and aerospace applications. These specific articles generally require very smooth surfaces combined with high temperature strength and resistance to stress fatigue. Applications include aircraft tail assemblies, leading edges and fairings. Polyepoxides, phenolics, isocyanates and bismaleimides represent examples of polymers which are cured by combining them with catalysts or hardeners to yield cured or cross-linked compositions. Typical hardeners or cross-linking agents which cure epoxy prepolymers are aliphatic and aromatic polyamines. Smith et al, U.S. Pat. No. 3,032,526, discloses the curing of a glycidyl polyether of a dihydric phenol with the reaction product of m-phenylenediamine and a dialkyl ketone. Ramos, U.S. Pat. No. 3,398,211, discloses synthetic resins derived from diglycidylethers of polyhydric alcohols interacting with diamines or hydroquinones and 1,4-cyclohexadiene dioxide. Labana et al, U.S. Pat. No. 3,714,120, discloses accelerators which are used to catalyze the curing of bisphenol A-epoxy type resins by aromatic diamines. Montesano, U.S. Pat. No. 3,316,191, discloses the curing of epoxy resins with tertiary amines in the presence of converters such as dodecenyl succinic anhydride. Kehr, U.S. Pat. No. 3,171,830, discloses a cross-linking process for solid olefin polymers containing carbonyl groups by subjecting said polymers to the action of hydrazine or a polyamine compound. Suzuki et al, U.S. Pat. No. 3,950,451, discloses a hardenable composition of an epoxy compound and a hardener produced by coupling a phenol, a diamine, formaldehyde or a functional derivative thereof and an alkylphenol. Current technology uses diamino diphenyl sulfone which is commonly referred to as DDS for curing epoxy resins to yield good mechanical properties of the cured part at elevated temperatures, e.g., Chemical Abstracts 89: 44579 m (Aponyi et al, Natl. SAMPE Symp. Exhib. 1978, 23, 479-89). However, sulfones in general, result in a cross-linked composition which has poor wet strength after being subjected to a wet or high humidity water environment.

Also, the cured compositions utilizing sulfones as the cross-linking agent have brittle failure characteristics or what is commonly described as a lack of toughness. This problem has been overcome to some extent by the addition of plasticizers, flexibilizers or elastomers which when admixed with the polymerizing resin increase fatigue resistance or brittle failure to some degree. These additives when used in combination with DDS cross-linking agent and a N,N,N',N'-tetraglycidyl-4,4'-diaminodiphenyl methane represent the current state of the art. A need therefore continues to exist for curative agents which will yield materials having excellent physical and mechanical properties.

SUMMARY OF THE INVENTION

Accordingly, one object of the invention is to provide a curative agent which will produce curable compositions having excellent physical and mechanical properties.

Another object of the invention is to provide curable compositions having excellent physical and mechanical properties.

Another object of the invention is to provide a process for curing such compositions.

A further object of this invention is to provide curable compositions which can be used in conjunction with fillers, reinforcements and extenders to yield a composite structure.

Briefly, these objects and other objects of the invention as hereinafter will become more readily apparent can be attained by providing a curative agent comprising a novel heterocyclic multifunctional amine adduct prepared by reacting at least one aromatic or aliphatic polyamine compound having at least two amine groups, which are separated by no more than one carbon atom, with at least one carbonyl-containing compound selected from the group consisting of aldehydes and ketones.

DETAILED DESCRIPTION OF THE PREFERRED EMBODIMENTS

It is common knowledge that amines react with ketones to form Schiff's bases or ketamines, e.g.,

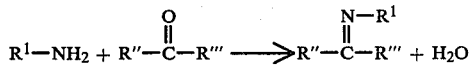

It is also know that 1,8-diamino-naphthalene will react with carboxylic acids and esters, in the present of an oxidizing agent to yield perimidines, Balasubramaniyan, Chem. Revs., 66, 6, pp 567.

The novel heterocyclic multifunctional amine adduct of the present invention is the reaction product of at least one aromatic or aliphatic polyamine compound having at least two amine groups, which are separated by no more than one carbon atom, with at least one carbonyl-containing compound selected from the group consisting of aldehydes and ketones. Suitable aldehydes correspond to the formula:

wherein R represents:

an alkyl group of one to twenty carbon atoms, which may be branched or unbranched, and which may be unsubstituted or substituted with an aldehyde group (—CHO) or a carboxyl group (—COOH);

an aromatic residue, preferably a phenyl group, which may be unsubstituted or substituted with an aldehyde group, a hydroxyl group or a lower alkoxy group of one to five carbon atoms. Examples of such aldehydes are terephtaladehyde, glyoxal, glutaraldehyde, glyoxylic acid, salicylaldehyde, vanillin and o-vanillin and heptaldehyde Suitable ketones correspond to the formula:

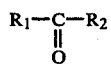

wherein $R_1$ and $R_2$ independently represent:

an alkyl group of one to twenty carbon atoms, which may be branched or unbranched, whose chain may be interrupted by one or more carbonyl groups

an aromatic residue, preferably phenyl; or $R_1$ and $R_2$ may together form a cycloaliphatic ring which may be interrupted by a carbonyl group; or $R_1$ and $R_2$ may together form an O-heterocyclic ring which may be substituted with lower alkyl group of one to five carbon atoms, hydroxyl group or acetyl group. Examples of such ketones are 2,4-pentanedione; 2,3-butanedione; benzil; 1,3-cyclohexanedione; acetone; 2-butanone; 2-heptanone; dehydroacetic acid and acetophenone.

Suitable polyamines are selected from: aliphatic polyamines having two to twenty carbon atoms corresponding to the formula:

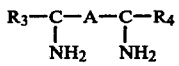

wherein A is a direct carbon-carbon bond or a —CH$_2$— group and $R_3$ and $R_4$ are independently hydrogen, alkyl groups which may be branched or unbranched and which may be unsubstituted or substituted with amine groups (—NH$_2$);

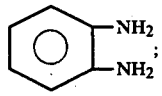 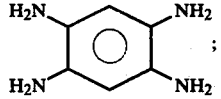

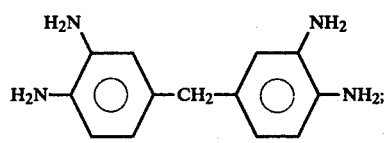

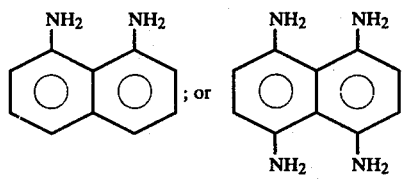

Examples of such polyamines are 1,3-diamino-propane; 1,2-diamino-benzene; 1,2,4,5-tetra amino-benzene; 3,3',4,4'-tetramino-diphenylmethane; 1,8-diamino-naphthalene and 1,4,5,8-tetra amino-naphthalene.

The heterocyclic diamine adducts of this invention may be prepared by reacting the aromatic or aliphatic polyamine compound having at least two amine groups, which are separated by no more than one carbon atom, with at least one carbonyl-containing compound selected from the group consisting of aldehydes and ketones at a temperature between room temperature and about 250° F., for convenience higher temperatures are preferred for increased speed of reaction, most preferably, at reflux temperature of the particular reaction mixture.

Any inert solvent, which will dissolve the reaction components can be used, for examples, alcohols such as ethanol or conventional industrial solvents such as methyl cellusolve.. Additionally, the carbonyl-containing compound, the aldehyde or ketone, may be used as a solvent. Alternatively, no solvent can be used, however, it is desirable to maintain the carbonyl to diamine molar ratio at 1:1 or in slight excess so as to ensure completion of reaction.

A catalyst may be present so as to increase the reaction rate. Any acid may be used, e.g. mineral acids such as hydrochloric acid or sulfuric acid and organic acids such as benzene disulfonic acid or p-toluene-sulfonic acid.

The heterocyclic diamine adduct may be recovered from the reaction mixture by cooling the same and recovering the precipitated product and then washing and/or drying the same. Alternatively, the reaction mixture may be drowned in water, the precipitated reaction product recovered by filtration and then washing and drying the precipitate.

Mixtures of polyamine compounds, mixtures of aldehydes, mixtures of ketones and/or mixtures of aldehydes and ketones may be used in the reaction to advantageously vary the properties of the heterocyclic diamine adduct.

Suitable compounds prepared by the above-noted technique include those corresponding to the formula:

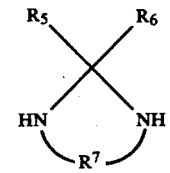

wherein $R_5$ and $R_6$ are independently selected from the group consisting of hydrogen, alkyl, phenyl,

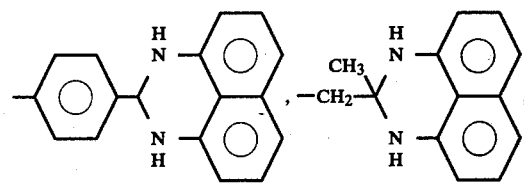

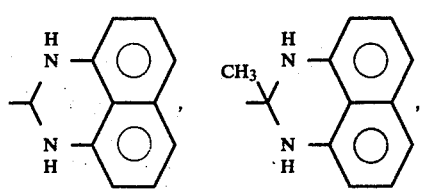

-continued

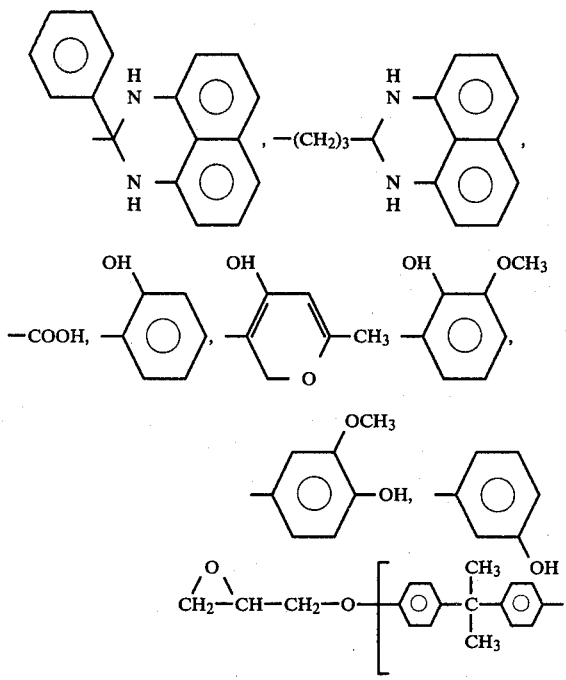

and $R_5$ and $R_6$ may jointly form

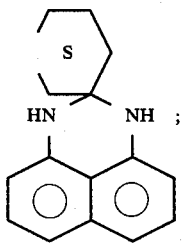

and $R_7$ is selected from the group consisting of:

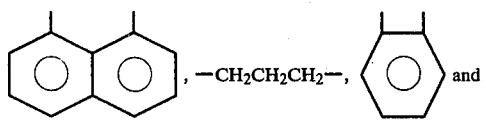

Particularly preferred diamine adducts are produced from 1,8-... nino-naphthalene and 1,3-diamino-propane.

The novel heterocyclic diamine adducts of this invention find particular use as curative agents in curable resin compositions. In particular, any resin reactive with an active hydrogen atom can be cured by the novel diamine adducts. Illustrative of such resins are the epoxy resins, phenolics, bismaleimide resins, isocyanates. Of particular importance are the epoxy resins.

Epoxy resins are compounds which contain an oxygen atom connected to two adjacent carbon atoms. A variety of epoxy resins are known and commercially available. Among the important groups of epoxy resins are those based on bisphenol A (4,4'-isopropylidine diphenol) and epichlorohydrin, novolacs and epichlorohydrin, aliphatic diepoxy ethers, aliphatic diepoxy esters, cycloaliphatic diepoxides, and 4,4'-methane dianiline and epichlorohydrin.

Epxoy resins of the type of diglycidyl ethers of bisphenol A are most easily available under trade names of Epon 828, Epon 1001, Epon 1002, Epon 1004, Epon 1007 from Shell Chemical Co. They are also available from Dow Chemical Co. with DER 331 as an example, or from Ciba Products Co. with Araldite 6010 as an example, or Celanese Epi Rez with Epi Rez 510 as an example. Their chemical structure corresponds to the formula:

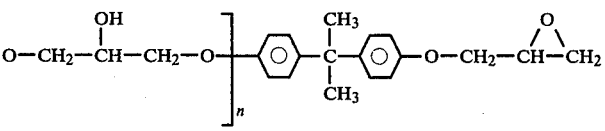

wherein n is the degree of the polymerization.

Novalac type epoxy resins are obtained by reacting novolacs, which are reaction products of phenol and formaldehyde, with epichlorohydrin and correspond to the general formula:

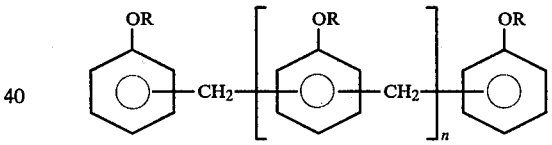

wherein R is

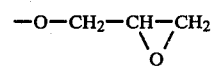

and n is the degree of polymerization. Cresol may be substituted in place of phenol to form the corresponding novolacs, of which an example is the ECN series from Ciba.

Aliphatic ether type epoxy resins are of the general formula:

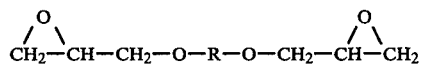

wherein R is a divalent alkyl group. While the formula shows two epoxy groups present, epoxy resins with more or less than two epoxy groups per molecule are also useful. An example of aliphatic ester type epoxy resin is diglycidyl adipate.

Cycloaliphatic type epoxy resins are those which contain oxygen atom attached to two adjacent carbon atoms which are part of ring containing other carbon, nitrogen and sulfur atoms. Examples of cycloaliphatic type epoxy resins are bis (2,3-epoxycyclohexanol) adipate and bis (2,3-epoxycyclopentyl) ether. A commercially available cycloaliphatic epoxy resin CY 178 from Ciba Products Co. is bis (2,3 epoxy-4-methylcyclohexanol) adipate.

An epoxy resin of the type of tetraglycidyl methane diamiline is available from Ciba Geigy under the trade name MY 720 and corresponds to the formula:

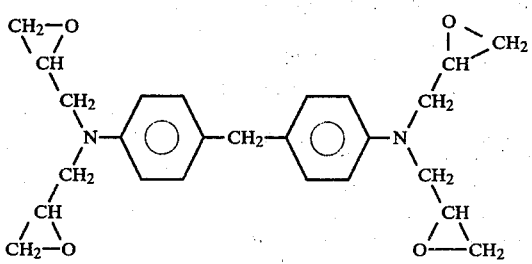

This resin is particularly preferred as it forms the basis of curable compositions of great utility in the aircraft and aerospace industry, e.g., structural composites of glass or graphite fibers.

Epoxy resins can also be prepared by copolymerization of unsaturated epoxy compounds such as glycidyl methacrylate with other vinyl monomers. The copolymerization conditions can be controlled to obtain polymers of widely different molecular weight, e.g., 2,000 to 100,000. Such vinyl polymerization techniques are well-known and conventional. The epoxy content of the copolymers can be controlled by using an appropriate amount of vinyl epoxy monomer, e.g., glycidyl methacrylate, relative to the amount of other monomer or monomers used.

The curable compositions of the present invention comprise a resin reactive with an active hydrogen atom, e.g., an epoxy resin, and the heterocyclic multifunctional amine adduct of this invention. The heterocyclic multifunctional amine adduct can be used in any amount in the curable composition, however, it is preferred to have a ratio of hydrogen equivalents of the adduct to reactive sites of the resin of 0.1-1.0, most preferably, the stoichiometric ratio or slightly thereunder. Additionally, mixtures of heterocyclic diamine adducts can be used as well as mixtures of resins, bearing in mind the desired stoichiometric ratio of active hydrogens and reactive sites.

Other ingredients may be included in the curable composition to advantageously influence the properties thereof.

A surfactant may be added, in amounts conventional in the art, to reduce the surface tension of the mixture. Illustrative of such surfactants are the siloxane-oxyalkylene block copolymers and vinyl silane-oxyalkylene graft copolymers and Triton X100 (Rohm & Haas —an octylphenoxy polyethoxyphenol surfactant).

A thixotropic agent may be added, in amounts conventional in the art, to control composition viscosity. The thixotropes may also function as fillers or extenders. Illustrative of such materials are mica, calcium carbonate, calcium phosphate, silica, glass, metal oxides, cellulose, starch, clays and diatomaceous earth.

Suitable catalysts may also be added, in conventional amounts, to provide a controlled and predictable composition cure rate. Catalysts can be from the family of latent hardeners such as boron trihalide complexes and dicyandiamide.

In addition, flexibilizing agents or elastomeric compounds, which may precipitate out as a second phase, may be incorporated into the composition to impart viscosity control along with producing increased toughness in the cured composition and thus inhibit fatigue and crack propagation. Illustrative of such flexibilizers or elastomers are acrylonitrile-butadiene copolymers, urethane elastomers and thermoplastic polymers, in general.

Alternatively, rather than use the heterocyclic diamine adduct, per se, in formulating the composition, it is possible to prepare the same in-situ by addition of the appropriate amounts of polyamine component and carbonyl-containing component. In this case, it is preferable to include an acid catalyst, as noted above, in the composition so as to reduce the reaction time necessary to form the heterocyclic diamine adduct.

It is also possible to incorporate the heterocyclic diamine adduct as a prepolymer, e.g., as the reaction product of the diamine adduct and a bismaleimide.

Curing of the composition is achieved by exposing the composition to sufficient energy to cause curing or cross-linking. The energy source may be heat or high energy radition such as microwave radiation. Typically, the composition is brought to a temperature of 350° F. or higher for 1 hour or more. Conventional post-cure treatments are also applicable to the composition of this invention.

Prior to curing or cross-linking, the curable composition can be applied to a reinforcing material. Such reinforcing materials may be in the form of woven, knitted or unidirectional parallel threads; filaments; yarns; or unwoven fibers made from either continuous or staple fibers. These reinforcements can be of organic or inorganic origin. Illustrative of such reinforcements are cotton, paper, fiberglass, polyesters, polyaramids, polyolefins, graphite, ceramics, metals and metal derivatives. Such reinforced compositions can be assembled as laminae to form a composite article which is subsequently cured. The resin composition can be applied to such reinforcements by techniques conventional in the art such as inpregnation, curtain coating, doctoring hot metal extrusion or callendering.

Having generally described this invention, a further understanding can be obtained by reference to certain specific examples which are provided herein for purposes of illustration only and are not intended to be limiting unless otherwise specified.

EXAMPLE 1

Product of 1,8-diamino-naphthalene and methyyl ethyl ketone

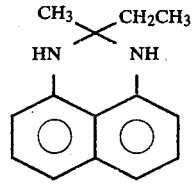

Into a flask, equipped with a stirrer, reflux condenser, thermometer well and addition port, is placed 152.8 grams (about a 6% excess) of methyl ethyl ketone and 0.8 gram of p-toluenesulfonic acid. The solution is stirred and 158.2 grams of 1,8-diamino-naphthalene is added over 30 minutes with sufficient cooling to allow the temperature to reach reflux (176° F.) at the end of the addition. The solution is then refluxed an additional 30 minutes. The yield is essentially guantitative. The reaction product may be isolated neat by evaporating off the excess methyl ethyl ketone and water, or it may be diluted further with acetone or more methyl ethyl ketone, mixed with other ingredients and used in a solvent coating application.

EXAMPLE 2

Reaction product of 1,8-diamino-naphthalene and terephthalaldehyde

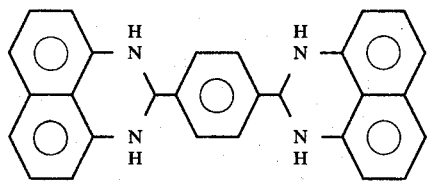

Into a beaker equipped with a stirrer and thermometer is placed 1000 ml of methyl cellusolve, 84.8 grams of terephthalaldehyde and 200 grams of 1,8-diaminonaphthalene. The mixture is heated and stirred to about 175° F. where a solution occurs. Then 0.4 grams of p-toluenesulfonic acid is added and stirring and heating are continued at 200°-240° F. for 1½ hours during which time the product precipitates out. The mixture is cooled, drowned into 3-4 times the volume of water, collected and dried in a 230° F. oven. The recovery is 244 gram (93% yield).

EXAMPLE 3

Reaction product of 2,4-pentanedione and 1,8-diamino-naphthalene

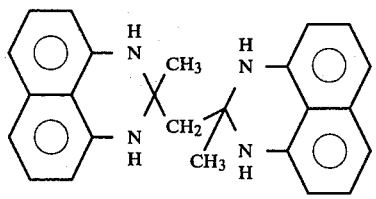

Into a flash, equipped with a stirrer, reflux condenser, thermometer well and addition port, is placed 66.7 grams 2,4-pentanedione and 1.0 gram of p-toluenesulfonic acid. 200 grams 1,8-diamino-naphthalene are added and the mixture is refluxed (pot temperature about 100° C.) and stirred for 2½ hours. It is then poured hot into trays and dried overnight at 230° F. to remove water and excess dione. The yield is essentially quantitative.

EXAMPLE 4

Reaction product of acetone and 1,3-diamino-propane

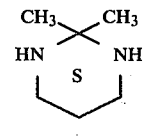

Into a flask, equipped with a stirrer, reflux condenser and addition port, is placed 58.1 grams of acetone and 0.3 gram of p-toluenesulfonic acid. 74.1 grams of 1,3-diamino-propane is added over 20 minutes with sufficient cooling such that the solution is at reflux (about 106°) at the end of the addition. The solution is refluxed an additional 1½ hours. The yield is essentially quantitative. Water contained in the product may be removed by distillation, if necessary.

EXAMPLE 5

Reaction product of 1,2-diamino-benzene and acetone 600 ml of acetone, 1 gram of paratoluenesulfonic acid and 200 grams of 1,2-diamino-benzene are stirred at reflux for 4 hours, cooled, drowned in 2500 ml of water, and the solid is collected and dried in a 180° F. oven. The yield is essentially quantitative.

EXAMPLES 6-21

In a similar manner, the following reaction products were prepared from the indicated components.

| Example No. | Reaction Product | Carbonyl-Containing Component | Diamine Component |
|---|---|---|---|
| 6 | | Glyoxal | 1,8-Diamino-naphthalene |

4,427,802
-continued
| Example No. | Reaction Product | Carbonyl-Containing Component | Diamine Component |
|---|---|---|---|
| 7 | 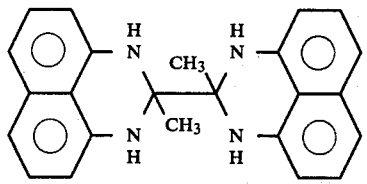 | 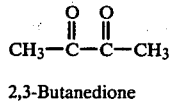 2,3-Butanedione | 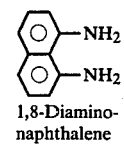 1,8-Diamino-naphthalene |
| 8 | 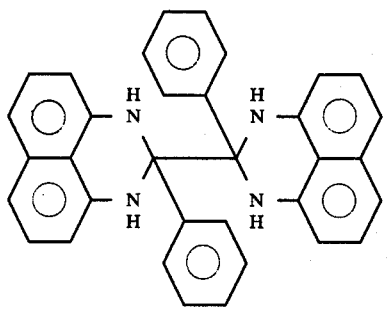 | 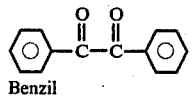 Benzil | 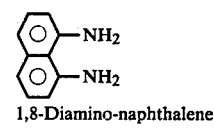 1,8-Diamino-naphthalene |
| 9 | 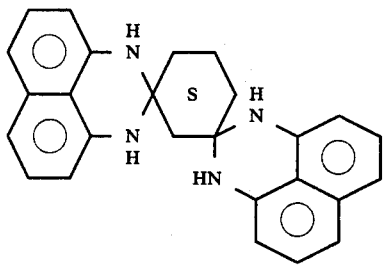 | 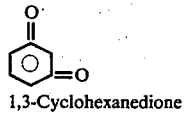 1,3-Cyclohexanedione | 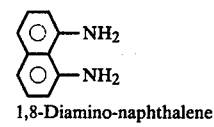 1,8-Diamino-naphthalene |
| 10 | 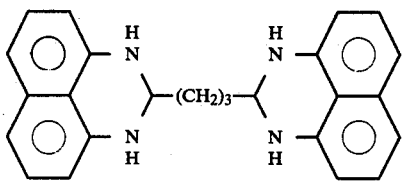 | 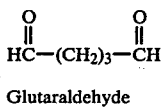 Glutaraldehyde | 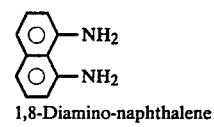 1,8-Diamino-naphthalene |
| 11 | 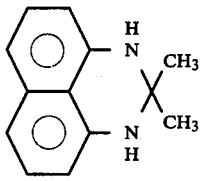 | 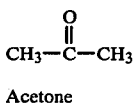 Acetone | 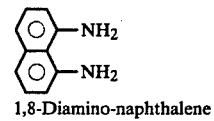 1,8-Diamino-naphthalene |
| 12 | 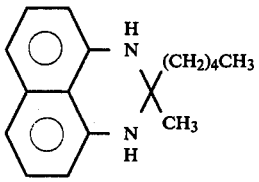 | 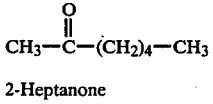 2-Heptanone | 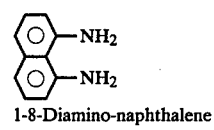 1-8-Diamino-naphthalene |

-continued

| Example No. | Reaction Product | Carbonyl-Containing Component | Diamine Component |
|---|---|---|---|
| 13 | (naphthalene fused with two NH groups bridging to CH-COOH) | HO-C(=O)-C(=O)H  Glyoxylic Acid | 1-8-Diamino-naphthalene |
| 14 | (naphthalene with two NH groups bridged to CH-(2-hydroxyphenyl)) | 2-hydroxybenzaldehyde  Salicyaldehyde | 1-8-Diamino-naphthalene |
| 15 | (naphthalene with two NH groups bridged to C(CH₃)-(dehydroacetic acid residue)) | Dehydroacetic Acid | 1-8-Diamino-naphthalene |
| 16 | (naphthalene with two NH groups bridged to CH-(2-hydroxy-3-methoxyphenyl)) | o-Vanillin | 1-8-Diamino-naphthalene |
| 17 | (naphthalene with two NH groups bridged to CH-(3-methoxy-4-hydroxyphenyl)) | Vanillin | 1-8-Diamino-naphthalene |
| 18 | (bis-phenyl methane with two C(CH₃)₂-NH and NH groups on each ring) | $CH_3-C(=O)-CH_3$  Acetone | 3,3',4,4'-Tetra amino-diphenyl-methane |
| 19 | (benzimidazoline with 2-hydroxyphenyl substituent) | Salicylaldehyde | 1-2-Diamino-benzene |
| 20 | (benzimidazoline with 3-methoxy-4-hydroxyphenyl substituent) | Vanillin | 1-2-Diamino-benzene |

| Example No. | Reaction Product | Carbonyl-Containing Component | Diamine Component |
|---|---|---|---|
| 21 | 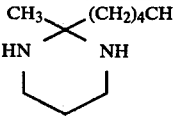 | $CH_3-\overset{O}{\underset{\|}{C}}-(CH_2)_4-CH_3$<br>2-Heptanone | $H_2N-(CH_2)_3-NH_2$<br>1,3-Diamino-propane |

EXAMPLE 22

Hot meltable resin system 66 grams of MY 720 (N,N,N',N'-tetraglycidyl-4,4'-diaminodiphenyl methane, made by Ciba Geigy Corp.) is heated to about 140° F. and 38.6 grams of the reaction product produced according to Example 3 is mixed in thoroughly by stirring. The mixture is cooled to below 120° F. and 1 gram of dicyandiamide (product of American Cyanamid) is mixed in. The mixture is roller milled and the resulting hot meltable resin system which is 100% solids (contains no volatiles) is coated on 7781 style woven glass, by conventional techniques, made into a 10 ply laminate and vacuum bag autoclave cured for 1½ hours at 350° F. by conventional techniques. No post cure was given. The following were the properties of the laminate:

| Thickness: | 92 mils |
|---|---|
| 350° F. Flexure Strength: | 76.4 ksi |
| 350° F. Flexure Modulus: | $3.52 \times 10^6$ psi |
| 350° F. Short Beam Shear: | 6.84 ksi |
| Voids: | void free |
| 350° F. Flexure Strength:<br>(after 96 hr. water boil) | 52.5 ksi |
| 350° F. Flexure Modulus:<br>(after 96 hr. water boil) | $2.79 \times 10^6$ psi |
| 350° F. Short Beam Shear:<br>(after 96 hr. water boil) | 3.45 ksi |

The uncured preimpregnated material had good initial tack and drape and retained it for at least 10 days storage at room temperature.

EXAMPLE 23

Solution coated resin system 16 grams of the reaction product, according to Example 1, is made by heating 11.9 grams of 1,8-diaminonaphthalene, 0.06 gram of p-toluenesulfonic acid and 339 grams of methyl ethyl ketone at near reflux for 30 minutes. The solution is cooled to under 140° F. and the following are added with stirring.

| 172 grams | MY 720 (Ciba Geigy) |
|---|---|
| 46 grams | diglycidyl aniline (Mobay) |
| 120 | reaction product of Example 2 |
| 2 grams | dicyandiamide (American Cyanamide) |
| 3 grams | 1001 CG (B. F. Goodrich, copolymer of butadiene and acrylonitrile, previously dissolved 15% by wt. in methyl ethyl ketone) |

The mixture is ball milled 2 hours, and results in a resin mixture of about 50% solids. 7781 style woven glass and Thornel T300 3K 12¼ by 12¼ square weave woven graphite cloth strips are solution coated with this resin using coventional techniques and the solvent is flashed off for 10 minutes at 190° F. in a circulating air oven.

The resin pick-up is about 35% and 37%, respectively. These are made into laminates and vacuum bag autoclave cured for 1½ hrs. at 350° F. using standard industry methods. No post cure was given. The following were the properties of the laminate:

|  | 7781 Glass | Woven Graphite |
|---|---|---|
| # of plies | 10 | 13 |
| Thickness (mils) | 92 | 105 |
| 350° F. Flexure Strength (ksi) | 76 | 65 |
| 350° F. Flexure Modulus ($\times 10^6$ psi) | 3.7 | 7.5 |
| 350° F. Short Beam Shear (ksi) | 6.25 | 5.5 |
| Voids | Void Free | Void Free |
| 350° F. Flexure Strength (ksi) after 96 hr. water boil | 56 | 37 |
| 350° F. Flexure Modulus ($\times 10^6$ psi) | 3.25 | 6.8 |
| 350° F. Short Beat Shear (ksi) after 96 hr. water boil | 4.2 | 3.55 |

The uncured preimpregnated material had good initial tack and drape and retained it for at least 10 days storage at room temperature.

EXAMPLE 24

Hot meltable resin system

This is the same resin system in Example 23, only a hot meltable version thereof, i.e. 100% solids—no volatiles. Warm together to about 140° F.:

| MY 720 | 145 grams |
|---|---|
| Diglycidyl aniline | 46 grams |
| My 720/1001 mix* | 30 grams |

(*made by dissolving 1 part 1001 CG (15% solution in methylethylketone) in 9 parts MY 720 and evaporating off the solvent)

and mix in:

| Reaction product of Example 2 | 120 grams |
|---|---|
| Reaction product (neat) of Example 1 | 16 grams |
| Dicyandiamide | 2 grams | and roller milled. This resin is hot melted, using conventional techniques, on to Thornel T300 3K graphite fibers with an aerial weight of 145 gm/m² to form a unidirectional preimpregnated material of about 33% net resin content. A 10 ply 0 degree unidirectional laminate was made and vacuum bag autoclave cured for 1½ hours at 350° F., by conventional techniques, which had the following properties:

| Thickness (mils) | 72 |
|---|---|
| 350° F. Flexure Strength (ksi) | 160 |
| 350° F. Flexure Modulus ($\times 10^6$ psi) | 17.9 |
| 350° F. Short Beam Shear (ksi) | 8.1 |

| | |
|---|---|
| Voids | Void Free |

The uncured preimpregnated material had good initial tack and drape and retained it for at least 10 days storage at room temperature.

EXAMPLE 25

Hot meltable resin system using a prepolymer 8.2 grams of

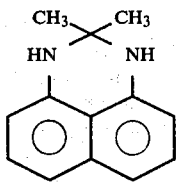

that is, the reaction product of 1,8-diamino-naphthalene with acetone, produced by the same procedure as in Example 1 only substituting acetone in place of methylethylketone, 30.5 grams of ERL 4206 (a cycloaliphatic epoxy made by Union Carbide), and 41.2 grams of 4,4'-bismaleimidodiplenylmethane are stirred and heated at 260° F. for 20 minutes. A linear prepolymer is formed from the maleimide and the reaction product of the 1,8-diamino-naphthalene with acetone and the reaction progress is monitored by High Pressure Liquid Chromatography as the reaction product peak disappears. The resin is cooled to about 150° F. and 20 grams of additional 4,4'-bismaleimidodiphenylmethane and 8 grams of the reaction product according to Example 2 were mixed in, followed by 0.4 gram of dicumyl peroxide at under 120° F. The mixture was roller milled thoroughly. This resin was hot melt coated on to 7781 style woven glass and Thornel T300 3K 12½ by 12½ square weave woven graphite, made into laminates, given a 2 hr., 375° F. vacuum bag autoclave cure, using conventional techniques, followed by a free standing 16 hr, 500° F. post cure for the woven graphite laminate and a 4 hr, 475° F. post cure for the glass laminate. The following were the laminate properties:

| | 7781 Glass | Woven Graphite |
|---|---|---|
| # of plies | 10 | 13 |
| Thickness (mils) | 92 | 82 |
| 500° F. Flexure Strength (ksi) | 52 | 53 |
| 500° F. Flexure Modulus ($\times 10^6$ psi) | 3.12 | 8.3 |
| 500° F. Short Beam Shear (ksi) | 3.75 | 4.1 |
| Voids | Void Free | Void Free |

Heat age 100 hr. @ 475° F., then:

| | Woven Graphite |
|---|---|
| 500° F. Flexure Strength (ksi) | 54 (1.6% wt. loss) |
| 500° F. Flexure Modulus ($\times 10^6$ psi) | 8.8 |
| 500° F. Short Beam Shear (psi) | 4.0 |

Having now fully described this invention, it will be apparent to one of ordinary skill in the art that many changes and modifications can be made thereto without departing from the spirit or scope of the invention set forth herein.

What is claimed as new and desired to be covered by Letters Patent is:

1. A curable composition comprising:

(A) an epoxy resin; and (B) a heterocyclic compound having the formula:

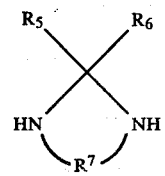

wherein $R_5$ and $R_6$ are each independently selected from the group consisting of hydrogen, alkyl, phenyl,

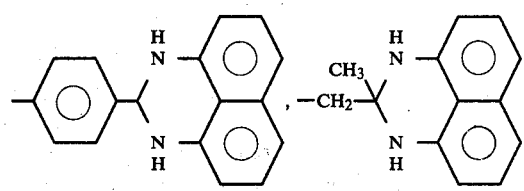

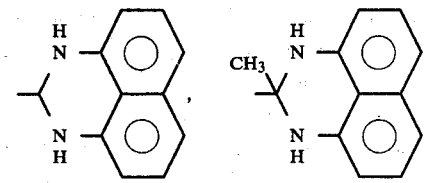

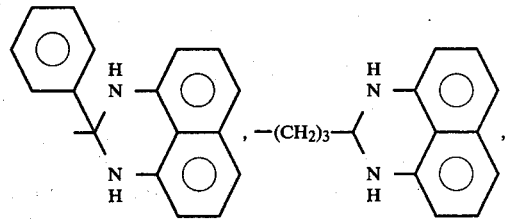

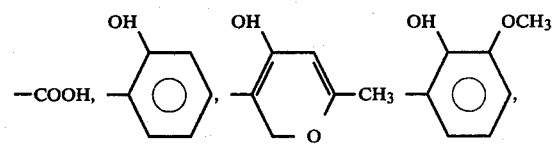

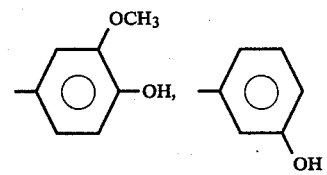

and $R_5$ and $R_6$ may jointly form

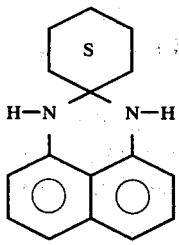

and R₇ is selected from the group consisting of

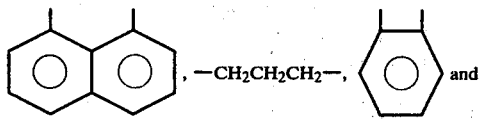

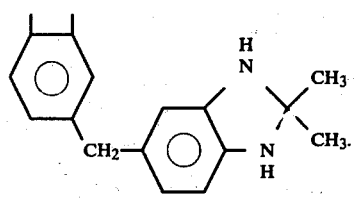

2. The curable composition according to claim 1, wherein the heterocyclic compound is the reaction product of at least one aromatic or aliphatic polyamine compound having at least two primary amine groups, which are separated by no more than one carbon atom, with at least one carbonyl-containing compound selected from the group consisting of aldehydes and ketones, wherein said polyamine is selected from:

aliphatic polyamines having 2-20 carbon atoms corresponding to the formula:

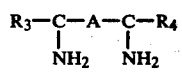

wherein A is a direct carbon-carbon bond or —CH₂— and R₃ and R₄ are each independently hydrogen or alkyl which may be branched or unbranched and which may be unsubstituted or substituted with amine groups;

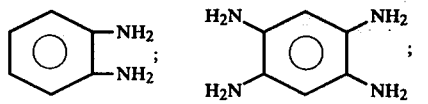

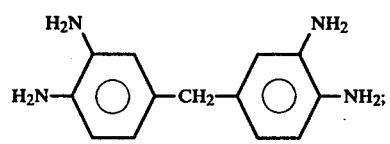

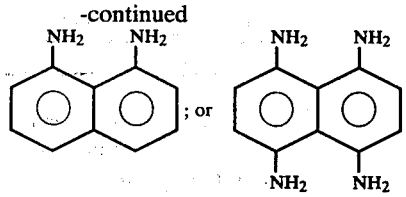

wherein said aldehydes correspond to the formula:

wherein R represents alkyl of 1-20 carbon atoms, which may be branched or unbranched, and which may be unsubstituted or substituted with —CHO or —COOH; —CHO; —COOH; or phenyl which may be unsubstituted or substituted with —CHO, —OH or lower alkoxy of 1-5 carbon atoms, and wherein said ketones correspond to the formula:

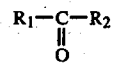

wherein $R_1$ and $R_2$ each independently represent alkyl of 1-20 carbon atoms, which may be branched or unbranched, and whose chain may be interrupted by one or more

groups; phenyl; or $R_1$ and $R_2$ may together form a cycloaliphatic ring which may be interrupted by

group; or $R_1$ and $R_2$ may together form an O-heterocyclic ring which may be substituted with lower alkyl of 1-5 carbon atoms, —OH or acetyl.

3. The curable composition according to claim 2 wherein the heterocyclic compound is formed in situ.

4. The curable composition of claim 2 wherein the heterocyclic compound is formed by reacting the polyamine and the carbonyl-containing compound in stoichiometric proportions.

5. The curable composition according to claim 1, wherein said epoxy resin is N,N,N',N'-tetraglycidyl-4,4'-diaminodiphenyl methane.

6. The curable composition according to claim 2, wherein the polyamine compound is selected from the group consisting of:
1,2-diamino-benzene;
1,8-diamino-naphthalene;
1,3-diamino-propane;
3,3',4,4'-tetra amino-diphenyl methane;
1,2,4,5-tetra amino-benzene; and
1,4,5,8-tetra amino-napthanlene.

7. The curable composition according to claim 2, wherein the aldehyde is selected from the group consisting of terephthalaldehyde; glyoxal, glutaraldehyde; glyoxylic acid; salicylaldehyde; vanillin and σ-vanillin.

8. The curable composition according to claim 2, wherein the ketone is selected from the group comprising:
   2,4-pentanedione;
   2,3-butanedione;
   benzil;
   1,3-cyclohexane-dione;
   acetone;
   2-butanone;
   2-heptanone;
   dehydroacetic acid; and
   acetophenone.

9. The curable composition according to claim 6, wherein the polyamine is 1,8-diamino-naphthalene.

10. The curable composition according to claim 6, wherein the polyamine is 1,3-diamino-propane.

11. The curable composition according to claim 7, wherein the aldehyde is terephthalaldehyde.

12. The curable composition according to claim 8, wherein the ketone is acetone.

13. The curable composition according to claim 8, wherein the ketone is 2,4-pentanedione.

14. The curable composition according to claim 2, which further comprises a reinforcing agent selected from the group consisting of cotton, paper, glass fiber, polyester fiber, polyaramid fiber, polyolefin fiber, graphite fiber and metal fiber.

15. The curable composition according to claim 14, wherein the reinforcing agent is graphite fiber.

16. The curable composition according to claim 15, wherein the graphite fiber forms a woven fabric.

17. The curable composition according to claim 14, which further comprises a surfactant.

18. The curable composition according to claim 14, which further comprises a thixotrope.

19. The curable composition according to claim 14, which further comprises a catalyst.

20. The curable composition according to claim 14, which further comprises an elastomer.

21. The curable composition according to claim 14, which further comprises a hardener.

22. A method of curing the curable composition according to claim 2, wherein the curable composition is subjected to sufficient energy to cause cross-linking.

23. The method of curing according claim 21, wherein the composition is heated.

24. The method of curing according to claim 21, wherein the composition is subjected to microwave radiation.

25. The curable composition according to claim 14, wherein the reinforcing agent is formed into laminae.

26. The composite article formed by curing the composition according to claim 25.

* * * * *